US00PP15945P2

(12) United States Plant Patent
Egger

(10) Patent No.: US PP15,945 P2
(45) Date of Patent: Sep. 6, 2005

(54) ***HEUCHERA* PLANT NAMED 'MARMALADE'**

(50) Latin Name: ***Heuchera* hybrid**
Varietal Denomination: Marmalade

(75) Inventor: Janet Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 105 days.

(21) Appl. No.: 10/871,960

(22) Filed: Jun. 18, 2004

(51) Int. Cl.[7] ..... A01H 5/00
(52) U.S. Cl. ..... Plt./263
(58) Field of Search ..... Plt./263

(56) References Cited

U.S. PATENT DOCUMENTS

PP13,348 P2 * 12/2002 Heims ..... Plt./263
PP15,085 P2 * 8/2004 Oliver ..... Plt./263

OTHER PUBLICATIONS http://www.blubprep.nl/greenteam/newplants/.*
http://www.terranovanurseries.com/pages/plantsH4.html.*

* cited by examiner

*Primary Examiner*—Kent Bell
*Assistant Examiner*—W. C. Haas
(74) *Attorney, Agent, or Firm*—Klarquist Sparkman, LLP

(57) ABSTRACT

A new and distinct hybrid of *Heuchera* plant characterized by russet to amber colored foliage, bold size and vigor.

1 Drawing Sheet

Botanical classification: *Heuchera* hybrid.
Variety denomination: 'Marmalade'.

The present invention relates to a new and distinct cultivar of *Heuchera* hybrid and given the cultivar name of 'Marmalade'. *Heuchera* is in the family Saxifragaceae. *Heuchera* 'Marmalade' originated from a cross between *Heuchera* 'Amber Waves', (U.S. Plant Pat. No. 13,348) as the seed parent, and *Heuchera* 'Huntsman' (unpatented) as the pollen parent. Given its ornamental foliage and flower form it is probable that *Heuchera micrantha, H. americana,* and *H. brizoides* are in its parentage.

This new *Heuchera* is distinguished by:

1. Russet to amber, wavy foliage year round.
2. Small white flowers on tall flowering stems.
3. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
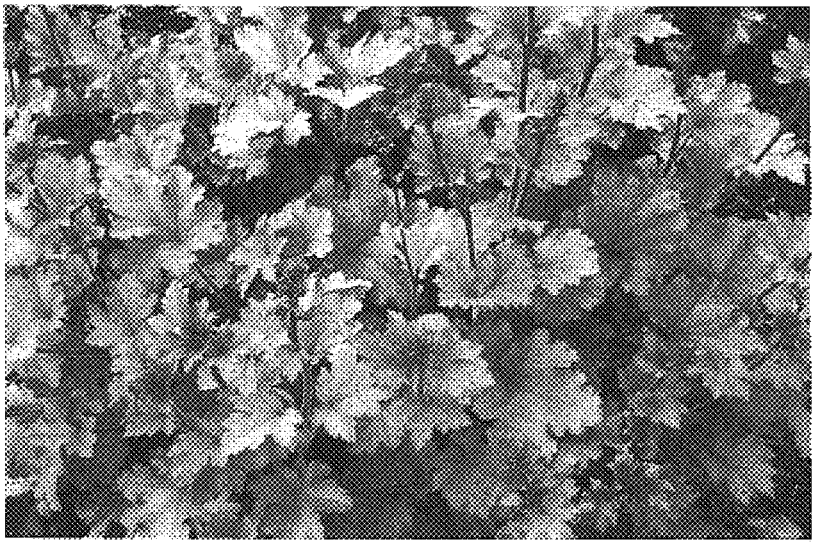
FIG. 1 shows new growth on a two year old plant of *Heuchera* 'Marmalade' growing in the ground in the shade house in spring in Canby, Oreg.
Figure 2:
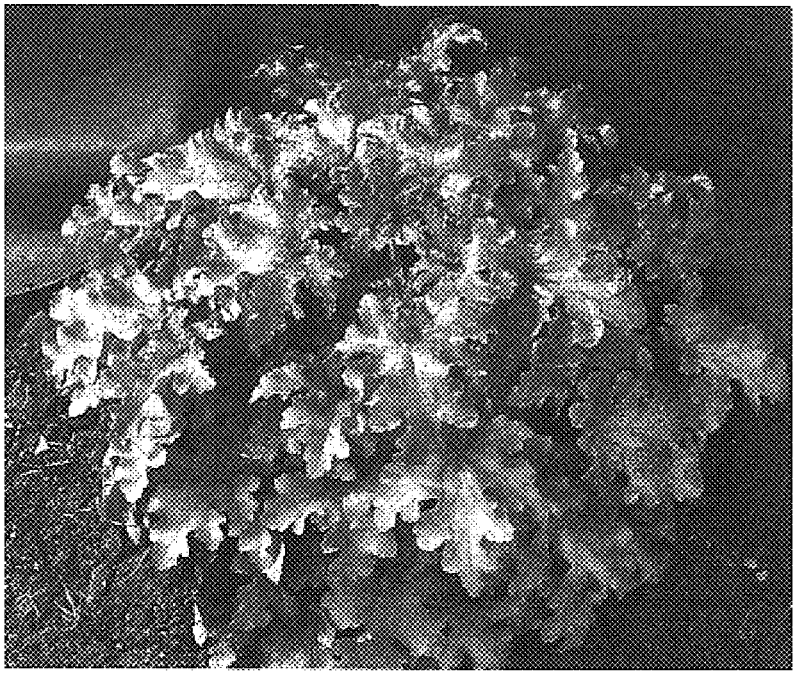
FIG. 2 shows a two year old plant of *Heuchera* 'Marmalade' growing in the ground in the shade house in late fall in Canby, Oreg.

The following is a detailed description of the new *Heuchera* cultivar based on observations of a two-year-old specimen grown in the ground in an open air shade house with 50% shade cover and added irrigation in the summer months in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Botanical classification: *Heuchera* hybrid.
Cultivar name: 'Marmalade'.
Parentage: *Heuchera* 'Amber Waves' U.S. Plant Pat. No. 13,348 (seed parent)×*Heuchera* 'Huntsman' (pollen parent).

Plant:
- *Form.*—Basal rosette, herbaceous perennial.
- *Hardiness.*—USDA Zone 4 to 9.
- *Size.*—30 cm tall from the ground to the top of the foliage and 57 cm wide.
- *Vigor.*—Excellent.
- *Roots.*—Fibrous, freely branching, fine, and white in color. Roots develop easily from cuttings.
- *Habit.*—Mounding.

Leaf:
- *Type.*—Simple.
- *Arrangement.*—Rosette.
- *Shape.*—Ovate.
- *Lobing/division.*—5 main lobes, with 1 to 2 shallow secondary lobes.
- *Venation.*—Palmate.
- *Margins.*—Crenate, incised and slightly undulate.
- *Apex.*—Mucronulate.
- *Base.*—Cordate, lobes sometimes slightly overlapping at the base.
- *Blade size.*—7 to 11 cm long and 7 to 10 cm wide.
- *Surface texture.*—Thin and leathery with glandular hairs on both the upper and lower surfaces.
- *Petiole size.*—16 to 19 cm and 2 to 3 mm wide.

*Petiole surface texture.*—Covered with glandular hairs of various sizes.

*Petiole color.*—Grayed Purple 186B to 184A.

*Leaf color.*—Spring abaxial — Yellow Green 152A on the oldest growth to Greyed Orange 164B to Greyed Orange 173A to Grayed Purple 183B on the newest growth. Spring adaxial — Grayed Purple 187C. Summer through winter abaxial — Yellow Green 152A on the lower leaves and Greyed Orange 173A on the upper. Summer through winter adaxial — Grayed Purple 187C. Veins — Same as the leaf color.

Inflorescence:

*Size.*—6 to 9 cm wide and 34 cm long.

*Type.*—Thyrse.

*Number of flowers.*—80 to 150 per thyrse.

*Number of thryse in spring.*—17.

*Peduncle.*—With 5 to 9 petiolate cauline leaves, orbicular to ovate, blades 2 to 5 cm long and 1 to 7 cm wide with an incised and crenate margin. Height — 61 to 78 cm. Diameter — 0.5 cm near base. Color — Greyed Purple 187B to D to 183A. Surface — Glandular pubescent.

*Branching.*—3 times.

*Pedicel.*—Length — Variable. Surface — Glandular hairs. Color — Grayed Purple 187B.

*Bloom period.*—May in Canby, Oreg.

Flower bud:

*Size.*—0.25 cm wide and 0.3 cm long.

*Description.*—Glandular puberulent, ovoid.

*Color.*—Overall Yellow Green 152D.

Flower:

*Type.*—Perfect, zygomorphic.

*Shape.*—Campanulate.

*Size.*—0.45 cm long and 0.3 cm wide.

*Petal count.*—5, inconspicuous.

*Petal color.*—White 155D on both surfaces.

*Petal description.*—Spatulate with a clawed base, curl back with age, acute apex, entire margin.

*Petal size.*—0.25 cm long.

*Calyx.*—5 lobes, ovate, divided ¼ way to the base, with glandular hairs.

*Calyx size.*—0.4 cm long and 0.3 cm wide.

*Calyx and flower color.*—Greenish White. Out and inside surfaces are Yellow Green 153A at base and Yellow Green 152A at the tips and Yellow White 158D in the middle. Outside surface is slightly darker overall.

*Pistil.*—One, typical of the genus, with the style 3 mm long and White 155B, 2-branched stigma White 155B, ovary greenish white, closest to Yellow Green 145D.

*Filiments.*—5 in number, each 4 mm long, White 155B.

*Anther.*—5 in number, oval, 0.3 mm long and 0.2 mm wide, color before dehiscence is Orange Red 24B, after dehiscence they are the color of their pollen.

*Pollen.*—Of moderate quantity, Orange 28A.

*Fragrance.*—None.

*Lastingness.*—Each thryse blooms for about 2 weeks on the plant.

Fruit:

*Type.*—Two-beaked ovoid capsule.

*Fertility.*—Good.

*Color.*—Brown 200D.

Seed:

*Shape.*—Linear.

*Size.*—2 mm. long.

*Color.*—Black. R.H.S. 202A.

Pest and disease tolerance: Excellent disease resistance to powdery mildew, the common problem of *Heuchera*. Susceptible to root weevils.

COMPARISON TO SIMILAR *HEUCHERAS*

Compared to *Heuchera* 'Amber Waves' (U.S. Plant Pat. No. 13,348), *Heuchera* 'Marmalade' has a much larger habit and size. The foliage of this new cultivar is less ruffled; larger, and darker with more pink tones overall.

I claim:

1. A new and distinct *Heuchera* plant as herein illustrated and described.

* * * * *